United States Patent
Alruhaimi

(10) Patent No.: US 10,028,807 B1
(45) Date of Patent: Jul. 24, 2018

(54) DENTAL APPLIANCE-HOLDING BRACKET ASSEMBLY

(71) Applicant: KING SAUD UNIVERSITY, Riyadh (SA)

(72) Inventor: Khalid Abdullah Ibrahim Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/789,511

(22) Filed: Oct. 20, 2017

(51) Int. Cl.
| A61C 7/16 | (2006.01) |
| A61C 7/28 | (2006.01) |
| A61C 7/22 | (2006.01) |
| A61K 6/00 | (2006.01) |

(52) U.S. Cl.
CPC .................. *A61C 7/16* (2013.01); *A61C 7/28* (2013.01); *A61C 7/22* (2013.01); *A61K 6/0023* (2013.01)

(58) Field of Classification Search
CPC .. A61C 7/18; A61C 7/282; A61C 7/12; A61C 7/14; A61C 7/28
See application file for complete search history.

(56) References Cited

U.S. PATENT DOCUMENTS

| 3,237,305 A * | 3/1966 | Hegedus .................. A61C 7/12 433/21 |
| 3,721,005 A * | 3/1973 | Cohen ...................... A61C 7/14 433/16 |
| 3,925,893 A | 12/1975 | Anderson |
| 3,946,488 A * | 3/1976 | Miller ..................... A61C 7/287 433/11 |
| 4,243,387 A | 1/1981 | Prins |
| 4,496,317 A | 1/1985 | Hulsey |
| 5,580,243 A * | 12/1996 | Bloore ..................... A61C 7/22 433/17 |
| 5,927,971 A * | 7/1999 | De Baets ............... A61C 7/282 433/17 |
| 6,033,217 A | 3/2000 | Shirasuka |
| 6,341,956 B1 | 1/2002 | Liou |
| 9,271,810 B2 | 3/2016 | Solano Reina et al. |
| 9,636,191 B2 | 5/2017 | Damon et al. |

(Continued)

FOREIGN PATENT DOCUMENTS

| FR | 2936701 | * 7/2013 |
| WO | WO 95/09580 A1 | 4/1995 |

OTHER PUBLICATIONS

40Pcs Dental 39.5 # Orthodontic Roth Buccal Tubes bands U / L First molar band. http://www.ebay.com/itm/40Pcs-Dental-39-5-Orthodontic-Roth-Buccal-Tubes-bands-Band-U-L-First-molar-TUS-/252499488007? ul=HN (Last Accessed on May 16, 2016) 4pgs.

*Primary Examiner* — Ralph Lewis
(74) *Attorney, Agent, or Firm* — Richard C. Litman

(57) ABSTRACT

The dental appliance-holding bracket assembly includes a plurality of housings attached to a corresponding tooth band, each of the tooth bands being cemented to the crown of an adjoining tooth. Each housing defines a socket of a ball-and-socket joint. The assembly further includes a plurality of bracket arms, each bracket arm having a shank including a proximal end and an opposing distal end. The proximal end of the shank has a ball pivotally captured within the housing socket to form a ball-and-socket joint, while the opposing distal end of the shank includes a ring adapted for supporting a dental appliance.

12 Claims, 10 Drawing Sheets

(56) References Cited

U.S. PATENT DOCUMENTS

| | | | |
|---|---|---|---|
| 2008/0293005 A1* | 11/2008 | Rahlis | A61C 7/02 433/16 |
| 2010/0304321 A1 | 12/2010 | Patel | |
| 2014/0205962 A1* | 7/2014 | Damon | A61C 7/14 433/13 |
| 2016/0128804 A1 | 5/2016 | Ji | |

* cited by examiner

DENTAL APPLIANCE-HOLDING BRACKET ASSEMBLY

BACKGROUND OF THE INVENTION

1. Field of the Invention

The disclosure of the present patent application relates to dental appliances, and particularly to a dental appliance-holding bracket assembly configured for supporting a traction bar for a curved anterior distractor, a fracture fixing bar, inter-maxillary fixation wires, and other dental appliances.

2. Description of the Related Art

Distraction osteogenesis is a process of lengthening bone in a gradual manner by distracting or separating one surgically sectioned bony part from an adjacent surgically sectioned bony part with the use of a distractor device. The distraction is typically performed in small daily increments, and generally results in the formation of new bone between the separated bony parts. The procedure is used to lengthen short bones or generate new bone in a defected or deficient bony site without the need for a bone graft.

However, distractor devices typically utilize holding plates and holding mesh to support a traction bar, wherein the holding plates and the holding mesh are submerged under the mucoperiosteum and, as such, require a surgical flap. See, for example, the inventor's prior U.S. Pat. No. 9,622,782, issued Apr. 18, 2017, which is hereby incorporated by reference in its entirety. Being submerged under the mucoperiosteum does not allow the surgeon to see or to easily control all the parts of the distractor. Further, having submerged holding plates and holding mesh requires that the patient undergo a second surgery upon completion of the distraction process.

Thus, a dental appliance-holding bracket assembly solving the aforementioned problems is desired.

SUMMARY OF THE INVENTION

The dental appliance-holding bracket assembly includes a plurality of housings attached to a corresponding tooth band, each of the tooth bands being cemented to the crown of an adjoining tooth. Each housing defines a socket of a ball-and-socket joint. The assembly further includes a plurality of bracket arms, each bracket arm having a shank including a proximal end and an opposing distal end. The proximal end of the shank has a ball pivotally captured within the housing socket to form a ball-and-socket joint, while the opposing distal end of the shank includes a ring adapted for supporting a dental appliance.

In the same way, the indirect fixation of facial bone fractures with a bar or wiring can be achieved utilizing the dental appliance-holding bracket assembly to hold the fixation bar or the wires.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
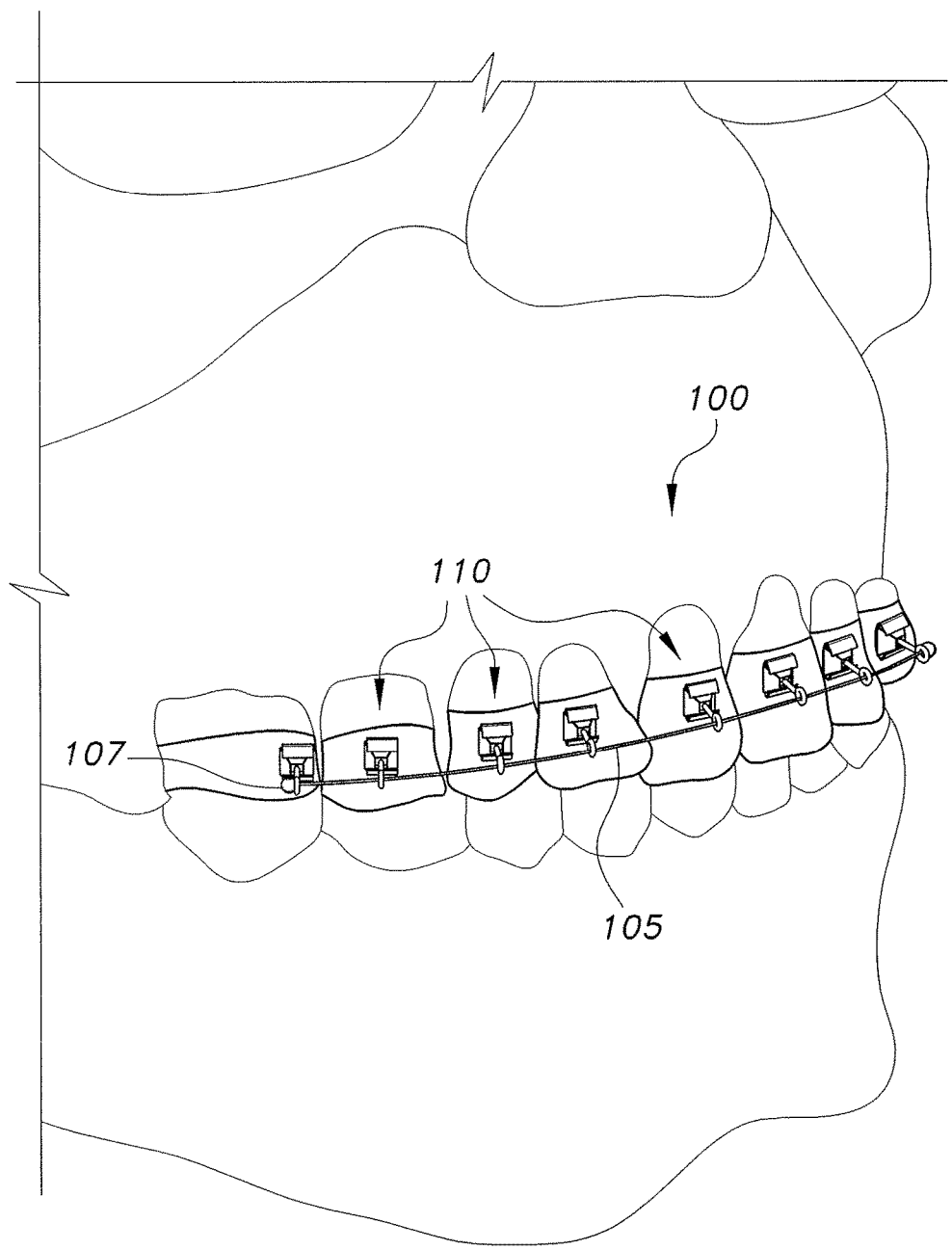
FIG. 1 is an environmental perspective view of a dental appliance-holding bracket assembly, shown supporting a dental appliance.
Figure 2:
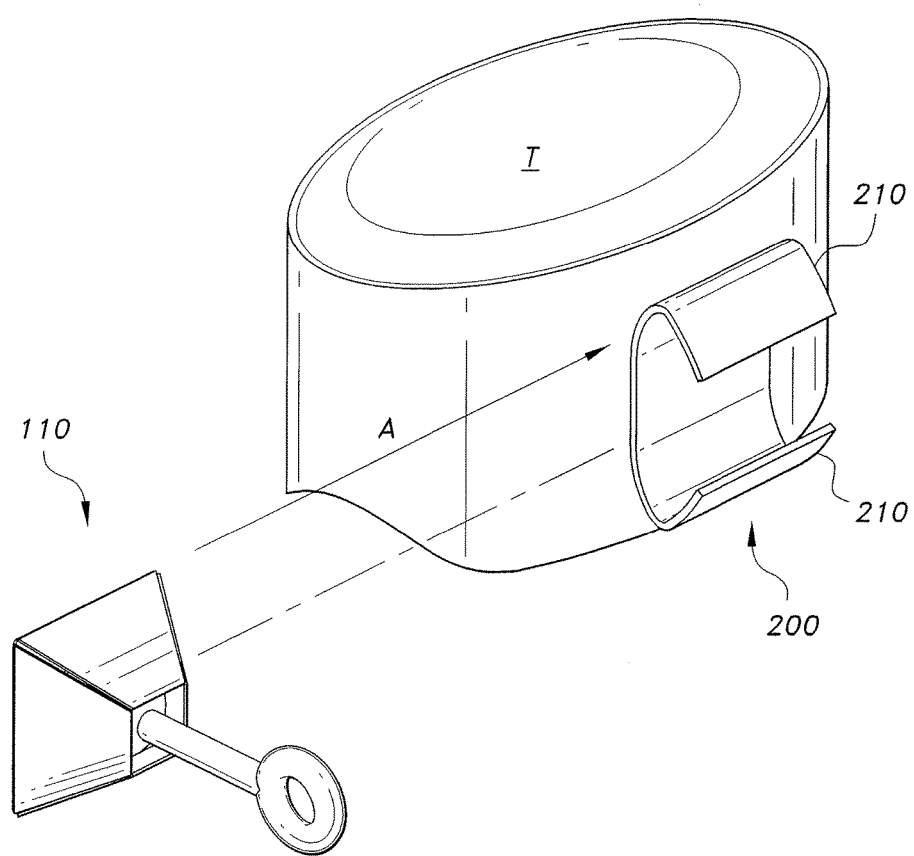
FIG. 2 is an exploded environmental perspective view of a bracket housing exploded from a tooth band.

Referring to FIGS. 1 through 9, a dental appliance-holding bracket assembly 100 for supporting a dental appliance 105, such as the traction bar of the curved anterior distractor device disclosed in U.S. Pat. No. 9,622,801, incorporated by reference in its entirety above, is generally illustrated. The assembly 100 may be used to support other types of dental appliances, such as a (closed) fracture fixing bar for indirect fixation for facial fracture, or indirect fixation with use of wire fixation or inter-maxillary wiring (used in closed fracture fixation), or to ensure correct occlusion in orthognathic surgery. The assembly 100 includes a plurality of housings 110, each housing 110 having a corresponding tooth band 200 attached thereto. Each tooth band 200 is secured onto the crown portion of a tooth T, e.g., by cement. The assembly 100 further includes a plurality of bracket arms 400, each bracket arm 400 having a shank 405 including a proximal end 407a and an opposing distal end 407b. The proximal end 407a of the shank 405 includes a ball 410 configured for capture within a socket defined by a housing 110 to form a ball-and-socket joint 500, while the opposing distal end 407b of the shank 405 includes a ring 415 configured for receiving the dental appliance 105.

Each housing 110 includes a base 600 having a substantially flat, square shape and a plurality of flaps 605 extending therefrom, each flap 605 being folded and joined together to form a prism-shaped housing 110. The base 600 includes a centralized spherical indentation 610 configured to act as part of the socket in the ball-and-socket joint 500. The base 600 may be formed from any suitable medical grade material, such as stainless steel, and may have any suitable thickness, such as a thickness of approximately 1 mm. The sides of the base 600 may have any suitable length, such as a length of approximately 3 mm. Each flap 605 may have any suitable shape, such as a generally triangular shape, such that when each of the flaps 605 is folder inward, such as toward the center of the base, a pyramid is formed. The prism-shaped base 600 defines a centrally located opening 510 configured for receiving the ball 410 of the bracket arm 400. The ball 410 is configured to act as the ball in the ball-and-socket joint 500 inside each corresponding housing 110.

The bracket arm 400 can be formed from any suitable type medical grade material, such as stainless steel. The shank 405, such as an elongated shaft, can have any suitable thickness, such as a thickness of approximately 1 mm, and any suitable length, such as a length between 2 mm and 3 mm. The ball 410 of the bracket arm 400 may have any suitable diameter, such as a diameter of approximately 2 mm. It is to be noted that the size of the centralized spherical indentation 610 is substantially equal to the size of the ball 410 of the bracket 400, such that the ball 410 may be positioned within the centralized spherical indention 610 of the base 600 and rotate freely within the centralized spherical indentation 610 of the base 600. The diameter of the central opening 510 defined by the housing 110 should be greater than the shank 405 to allow the bracket arm 400 to rotate freely in all directions within the housing 110, so that the ring 415 at the distal end may describe a circular arc when the bracket arm is pivoted.

The free rotation of the bracket arms 400 may facilitate leveling of each bracket arm 400, and in turn, facilitate passage of the dental appliance 105 through the ring 415 at the distal end of the bracket arm 400. The ring 415 of the bracket arm 400 has any suitable thickness, such as a thickness of approximately 1 mm, and an aperture 417 having any suitable diameter, such as a diameter between 1 mm to 2 mm, depending on the thickness of the dental appliance 105, which passes through the aperture 417 of the ring 415 of each bracket arm 400.

Figure 3A:
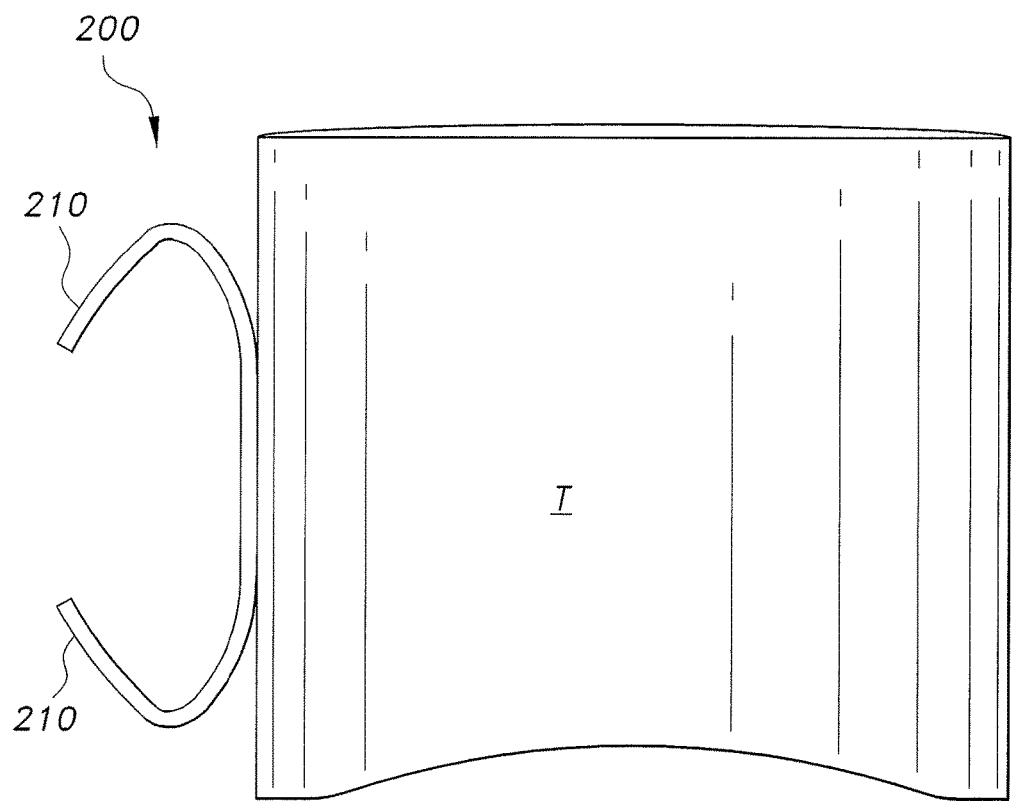
FIG. 3A is an environmental side view of a tooth band attached to a tooth.

Each of the tooth bands 200 is formed from any suitable medical grade material, such as stainless steel. The tooth bands 200 may come in a variety of different sizes to fit onto crown portions of different shapes and sizes, such that each tooth band 200 may be selected according to the size of the crown portion of the tooth T without having to cut and/or reshape the crown portion of the tooth T for the fitting. For example, the tooth band 200 may have a height of approximately 6 mm and a thickness of approximately 0.5 mm to allow for easy adaptation around the crown portion of a selected tooth T. The tooth band 200 may be affixed onto the crown portion of the tooth T with any suitable crown cement already known in the art, as illustrated in FIG. 3A. A slot frame 210 is formed or welded onto each tooth band 200, and the sides may have a length of approximately 3 mm to receive the base 600 of a corresponding one of the bracket housings 110.

Figure 6A:
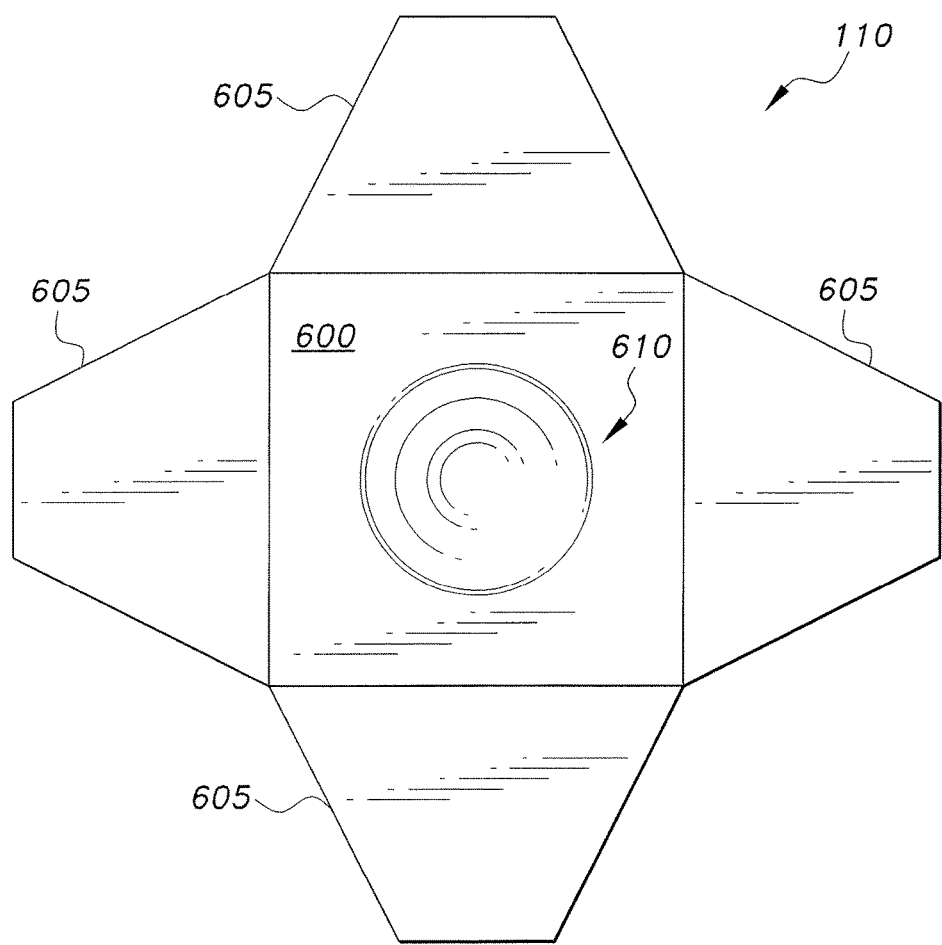
FIG. 6A is a top view of a bracket housing, shown before assembly.
Figure 6B:
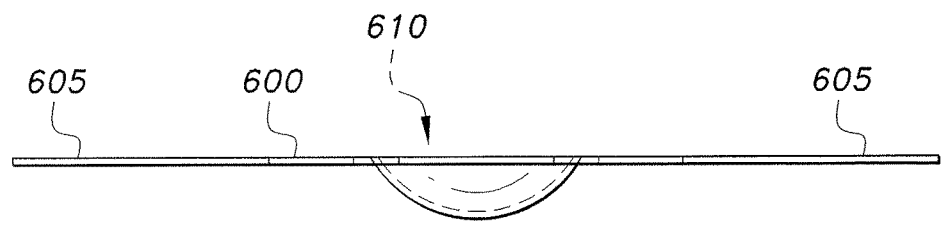
FIG. 6B is a side view of the unassembled bracket housing of FIG. 6A, showing spherical indentation of the base.

By way of operation, to form the ball-and-socket joint 500 within each of the bracket housings 110, the ball 410 positioned at the proximal end 407a of the shank 405 is first positioned within the centralized, spherical indentation 610 of the base 600 of each housing 110 while each of the flaps 605 are open (i.e., lying flat on a surface, as shown in FIG. 6A). Each of the flaps 605 is then folded inward to form the prism, which forms the ball-and-socket joint 500. Each flap 605 is then secured, such as welded, to the adjacent flap 605 to seal the housing 110 and allow only the portion of the shank 405 attached to the ring 415 to extend outward through the opening 510 from the corresponding housing 110.

Figure 5:
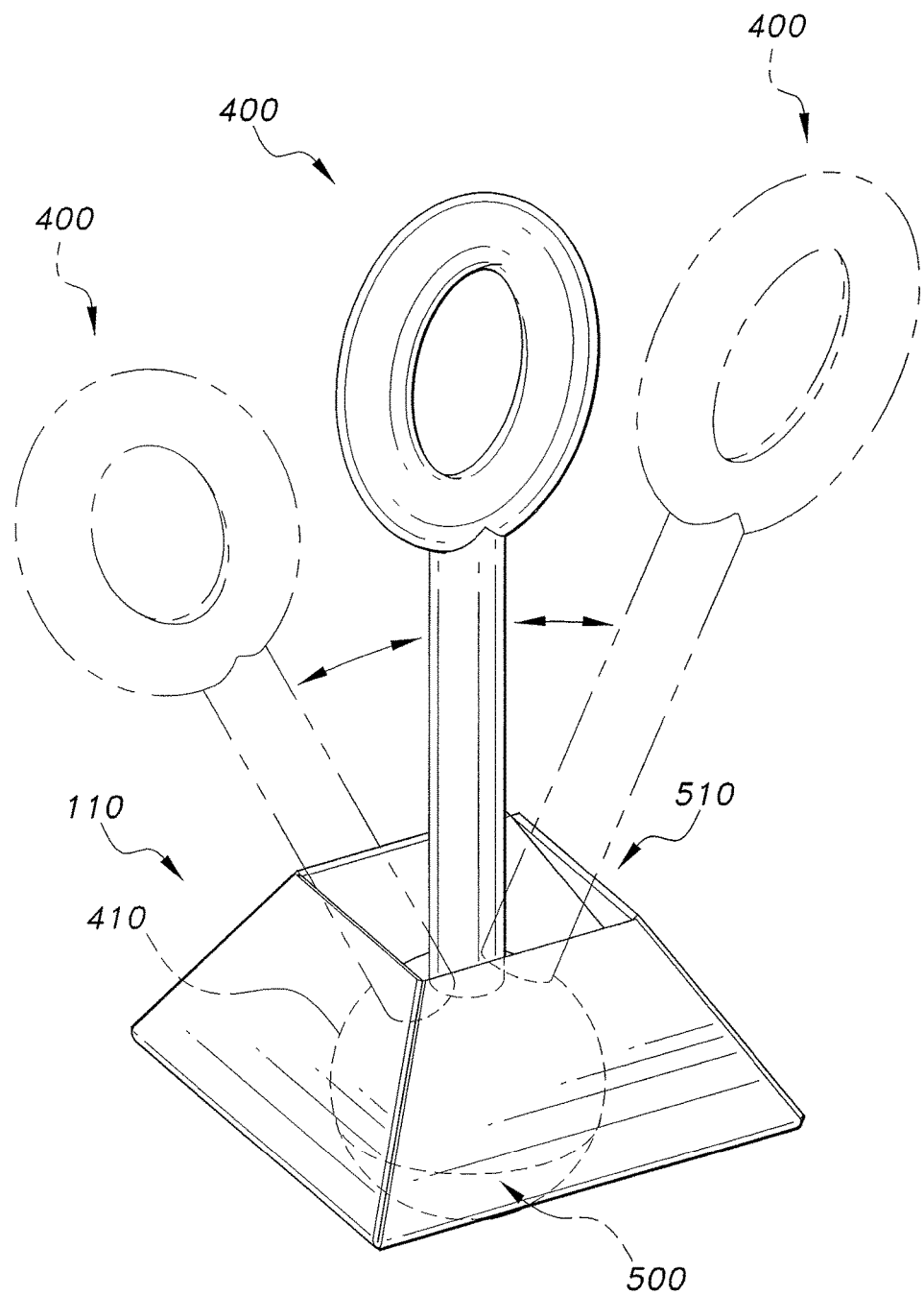
FIG. 5 is a perspective view of a bracket arm shown pivotally mounted to a bracket housing.

Securing each flap 605 to one another secures the ball 410 within the corresponding housing 110 and prevents the ball 410 from sliding out of the housing 110 (i.e., the ball-and-socket joint) while rotating. The movement (e.g. rotation) of each bracket arm 400, as shown in FIG. 5, allows the surgeon to level all the bracket arms 400, even if the patient's teeth are not level, in order to facilitate the passage of the appliance 105 through the aperture 417 of each ring 415 of each bracket arm 400 along the arch formed by the teeth, as illustrated in FIG. 1. This process is repeated until a sufficient number of housings 110 containing bracket arms 400 have been assembled.

Figure 3B:
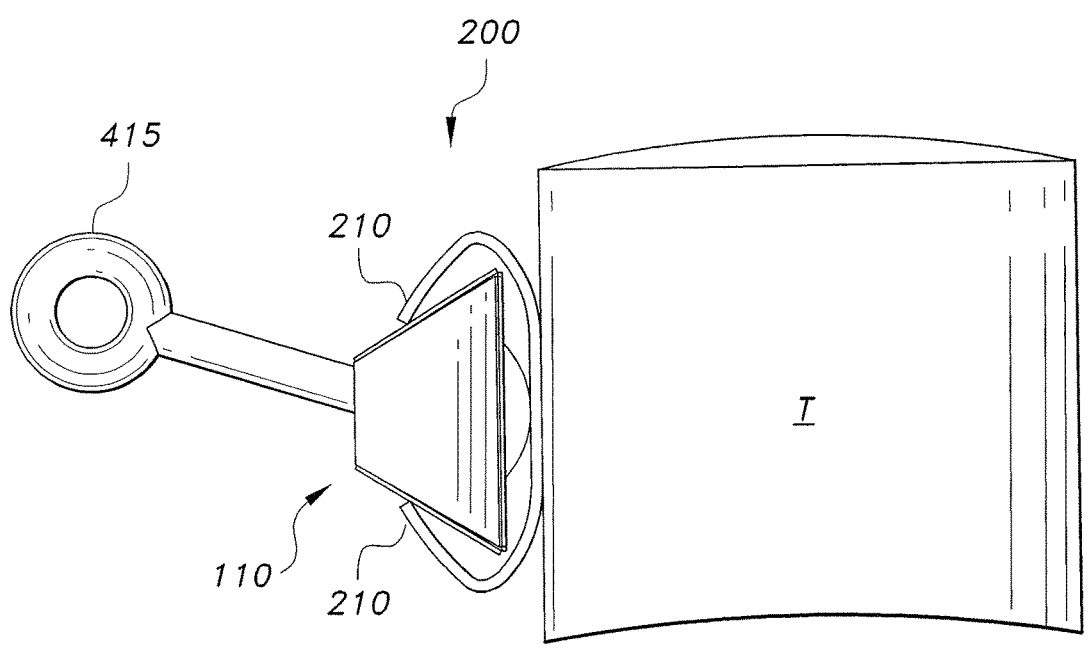
FIG. 3B is an environmental side view of a tooth band attached to a tooth, a bracket housing inserted into the tooth band, and a bracket arm mounted on the bracket housing.
Figure 4:
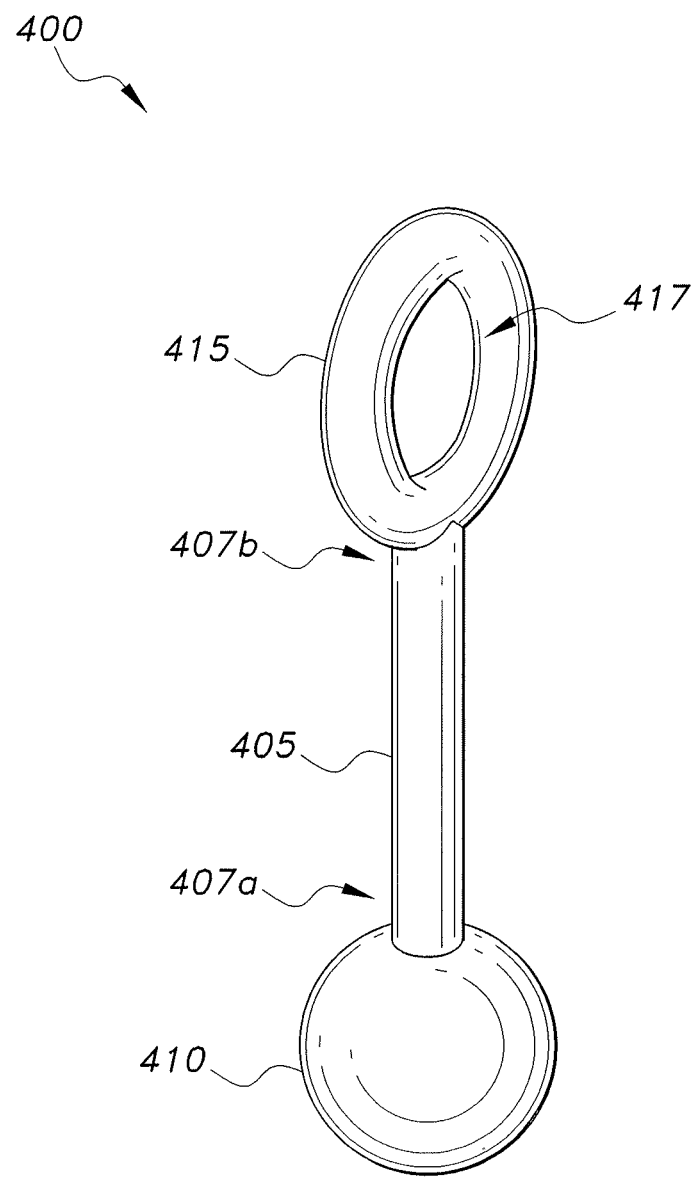
FIG. 4 is a perspective view of a bracket arm of the dental appliance-holding bracket assembly.

Once a sufficient number of housings 110 including bracket arms 400 have been assembled, the operator must then select the tooth band 200 corresponding to the size of the crown portion of the tooth T on which the tooth band 200 will be attached. The operator must then attach, e.g., using cement, one tooth band 200 to the crown portion of each tooth T involved in the procedure, as illustrated in FIGS. 3A and 3B. The base 600 of each housing 110 is then inserted into the slot fame 210 of each tooth band 200 already secured onto the crown portion of the tooth T. It is to be noted that the slot frame 210 of each tooth band 200 has a width similar to the width of the base 600 of each housing 110 to allow for easy sliding, into and out of the tooth band 200, as shown by arrow A in FIG. 2, but also allows each tooth band 200 to hold the corresponding housing 110 in position after insertion.

After the base 600 of each housing 110 has been inserted and secured into the slot frame 210 of each corresponding tooth band 200, the orthodontic appliance 105 is inserted through the aperture 417 of the ring 415 of each bracket 400 from one end of the dental arch to the other. Once the dental appliance 105 has been inserted through the aperture 417 of each ring 415 of each bracket arm 400, the operator may check the stability and the level of the bracket arms 400 that support the dental appliance 105. It is to be noted that an anchor 107 may be secured to both ends of the dental appliance 105 to secure the appliance 105 to the assembly 100.

Figure 7:
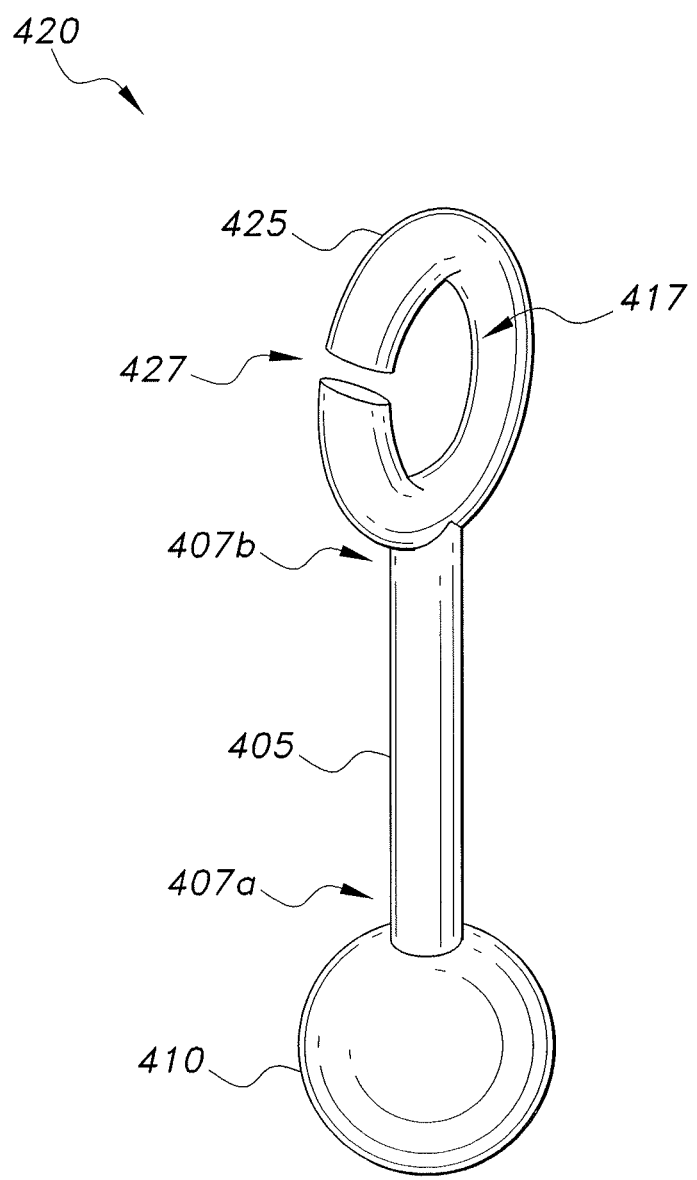
FIG. 7 is a perspective view of an alternative embodiment of a bracket arm of a dental appliance-holding bracket assembly.
Figure 8:
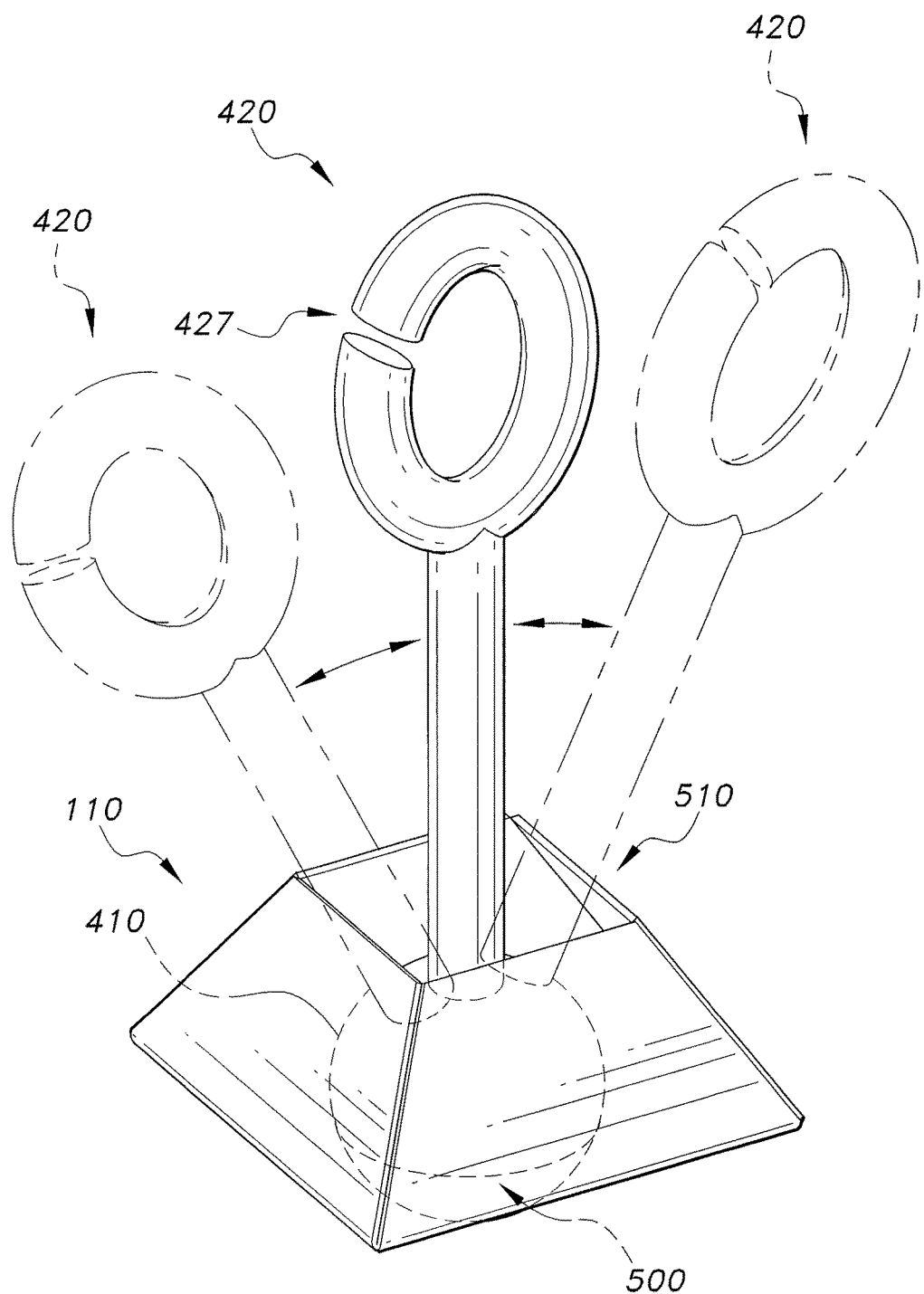
FIG. 8 is a perspective view of the bracket arm of FIG. 7 shown pivotally mounted to a bracket housing.

An alternative bracket 420, shown in FIG. 7, can be used in conjunction with the housing 110. The alternative bracket 420 is substantially similar to bracket 400. The difference between bracket 400 and bracket 420 is that the alternative bracket 420 includes a ring 425 having a slot or opening 427 along the circumference of the ring 425, as shown in FIGS. 7 and 8.

Figure 9:
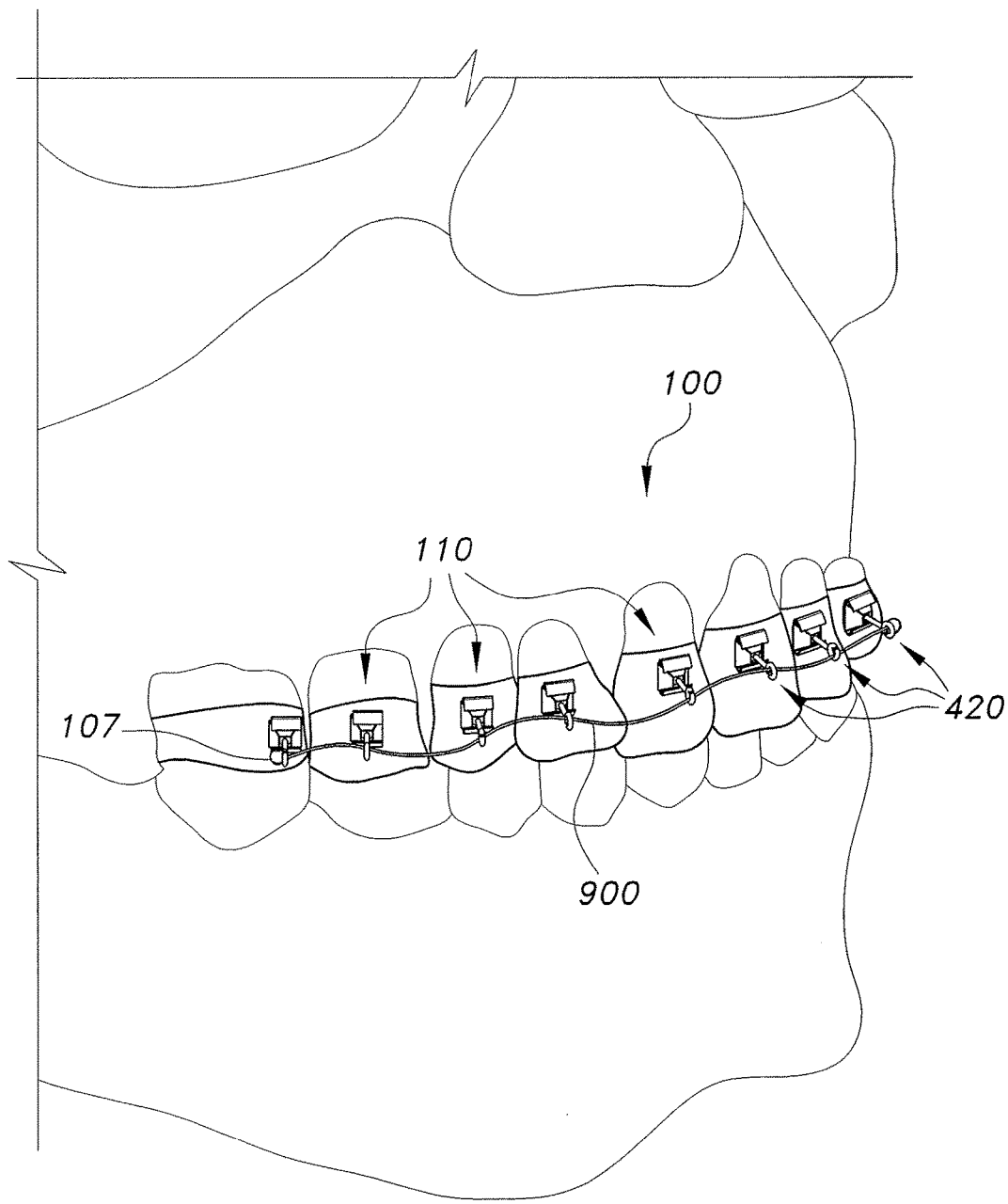
FIG. 9 is an environmental perspective view of a dental appliance-holding bracket assembly, shown supporting inter-maxillary fixation wires.

The operator may use this opening 427 to pass a wire 900, such as an inter-maxillary fixing wire, through each ring 425 in the dental arch, wherein the position of the opening 427 in the ring 425 is opposite to the position of the opening 427 in the adjacent ring 425 to allow the operator to pass the wire 900 up and down through the aperture 417 of each ring 425, as shown in FIG. 9, to increase the tension on the wire.

It is to be understood that the dental appliance-holding bracket assembly is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A dental appliance-holding bracket assembly, comprising:
   a plurality of bracket housings, each of the housings having a first length, each of the housings consisting of a top, side surfaces and a base surface defining a socket, wherein the side surfaces define a truncated pyramid and the base includes a central spherical indentation;
   a plurality of C-shaped tooth bands, each of the tooth bands defining a slot, each of the tooth bands having a corresponding one of the housings slidably retained in the slot, the tooth bands being adapted for attachment to the crown portion of a tooth; and a plurality of bracket arms, each of the bracket arms including a shank having a proximal end and a distal end, each of the bracket arms having a second length wherein the second length is greater than the first length of the housing, the proximal end having a ball sized and configured to be captured within the socket of a corresponding one of the bracket housings and to engage a corresponding spherical indentation thereby forming a ball-and-socket joint and the distal end having a ring adapted for supporting the dental appliance when the appliance is extended through the rings of the bracket arms.

2. The dental appliance-holding bracket assembly according to claim 1, wherein the appliance is selected from the group consisting of a traction bar, a fracture fixing bar, and inter-maxillary fixation wire.

3. The dental appliance-holding bracket assembly according to claim 1, wherein each of the housings has a base having a thickness of about 1 mm.

4. The dental appliance-holding bracket assembly according to claim 3, wherein the base is rectangular and has sides having a length of about 3 mm.

5. The dental appliance-holding bracket assembly according to claim 4, wherein each side of the base has a triangular flap extending therefrom, the flaps being folded and joined so that said housing is prism-shaped.

6. The dental appliance-holding bracket assembly according to claim 1, wherein the ring at the distal end of said bracket arm is capable of describing a circular arc when said bracket arm is pivoted.

7. The dental appliance-holding bracket assembly according to claim 1, wherein the shank of each bracket arm has a length between 2 mm and 3 mm.

8. The dental appliance-holding bracket assembly according to claim 1, wherein the ball of each bracket arm has a diameter of about 2 mm.

9. The dental appliance-holding bracket assembly according to claim 1, wherein the ring of each bracket has a thickness of about 1 mm.

10. The dental appliance-holding bracket assembly according to claim 1, wherein the ring of each bracket defines an aperture having a diameter between 1 mm and 2 mm.

11. The dental appliance-holding bracket assembly according to claim 1, wherein the ring describes a continuous loop.

12. The dental appliance-holding bracket assembly according to claim 1, wherein the ring is a split ring, having a slot defined therein.

\* \* \* \* \*